United States Patent [19]

Reiss

[11] Patent Number: 5,601,094

[45] Date of Patent: Feb. 11, 1997

[54] OPHTHALMIC SHUNT

[76] Inventor: George R. Reiss, 4711 E. Cochise Dr., Phoenix, Ariz. 85028-4223

[21] Appl. No.: 346,213

[22] Filed: Nov. 22, 1994

[51] Int. Cl.$^6$ .................................................. A61M 27/00
[52] U.S. Cl. ................................................ 128/899; 604/8
[58] Field of Search ........................ 128/899; 604/8–10; 623/4–6

[56] References Cited

U.S. PATENT DOCUMENTS

| | | | |
|---|---|---|---|
| 4,729,761 | 3/1988 | White | 604/8 |
| 5,338,291 | 8/1994 | Speckman et al. | 604/8 |
| 5,397,300 | 3/1995 | Baerveldt et al. | 604/8 |

*Primary Examiner*—Angela D. Sykes
*Assistant Examiner*—Samuel Gilbert
*Attorney, Agent, or Firm*—Banner & Witcoff, Ltd.

[57] ABSTRACT

The invention is directed to an ophthalmic shunt implantable in a human eye. The shunt includes a central portion, an anterior tab extending from one end of the central portion and a posterior tab extending from an opposite end of the central portion. The tabs are disposed at an angle to the central portion. When the shunt is implanted, the curvature substantially corresponds to the exterior curvature of the eye at and adjacent to the location of the limbus, and the overall length of the shunt is sufficient to allow the anterior tab to be disposed intracorneally and the posterior tab to extend into a suprachoroidal space formed between the sclera and the choroid. During implantation, an opening is formed at the location of the limbus and extends into the anterior chamber of the eye. The shunt is disposed to bridge the opening and maintains a gap above the opening. Accordingly, the aqueous fluid from the anterior chamber flows along the shunt and into the suprachoroidal space, thereby reducing the intraocular pressure.

16 Claims, 6 Drawing Sheets

OPHTHALMIC SHUNT

BACKGROUND OF THE INVENTION

1. Field of the Invention

The present invention is directed to an ophthalmic shunt for treating glaucoma by draining fluid from the anterior chamber of the eye.

2. Description of the Prior Art

Glaucoma is a blinding disorder caused by optic nerve damage resulting from elevated intraocular pressure. The elevated pressure is a direct result of the inability of the eye to drain the aqueous humor fluid from the anterior chamber of the eye, which is formed between the lens-iris plane and the cornea. Aqueous fluid is created by the ciliary body, and serves to provide nutrients for the lens and to carry away waste products resulting from the metabolism of the surrounding tissues. In a normal eye, the aqueous produced by the ciliary travels through the pupil into the anterior chamber, is removed through the trabecular meshwork, and passes through Schlemm's canal and into blood vessels. The balanced flow and removal of aqueous fluid to and from the anterior chamber allows for maintenance of a healthy intraocular pressure. However, if the necessary rate of outflow is not maintained, for example, due to an obstruction of the trabecular meshwork, fluid buildup in the anterior chamber occurs. This results in intraocular pressure elevation, and the optic nerve may be damaged.

Prior art devices for treating glaucoma include a variety of implants which allow aqueous fluid to flow from the anterior chamber, bypassing the trabecular meshwork, and thereby relieving the intraocular pressure. For example, U.S. Pat. No. 4,521,210 to Wong discloses an implant device shaped as a cruciform, including a main stem portion and an integral cross arm. The front end of the device has a sharp edge. The device is curved along its length so as to allow the device to lie against the interior surface of the sclera when implanted. The device is implanted by creating a scleral flap adjacent the ciliary body which is retracted to expose a scleral bed. Two incisions are made through the bed. The sharp-edged front end of the device is inserted into the forward incision to separate the sclera from the ciliary body, with the forward edge extending into the anterior chamber and disposed adjacent the inner layers of the cornea. The rearward edge is inserted into the suprachoroidal space between the sclera and choroid, and the scleral flap is sutured over the implant.

The device of Wong relieves pressure in the anterior chamber by allowing aqueous fluid to flow from the anterior chamber along the length of the implant and into the suprachoroidal space, where it is absorbed into the blood system. However, since Wong's device extends within the anterior chamber adjacent to the inner surfaces of the inner corneal layers, it may come into contact with the sensitive inner corneal layer, that is, the endothelium. Irritation of and possible damage to the endothelium may result. Further, Wong's device is disposed entirely within the eye, making the implantation thereof a relatively complicated procedure, and also making it impossible to control the rate of fluid flow from the anterior chamber to the suprachoroidal space after implantation.

U.S. Pat. No. 4,946,436 to Smith discloses an implant device which is placed in a pocket made in the sclera. The implant includes a porous interior. To insert the device, both an upper and lower flap of the sclera are raised into the cornea. The inner flap of sclera is then excised at the approximate location of the limbus, allowing access to the anterior chamber. The implant is disposed over the opening in the pocket created in the sclera by removal of the flaps, with the anterior portion of the device anchored in a lamellar shelf created in clear cornea.

In Smith, the aqueous fluid is carried to the sclera by the porous interior of the implant. No suprachoroidal space is created for receiving fluid flow since Smith's implant is not long enough to extend into the suprachoroidal space. Further, since the implant is made of a porous hydrogel material, it is not rigid enough to maintain such a space.

SUMMARY OF THE INVENTION

The present invention is directed to an ophthalmic shunt implantable in a human eye. The eye includes, among other parts, a sclera, a limbus, a cornea and a choroid. The shunt includes a central portion, an anterior tab extending from one end of the central portion, and a posterior tab extending from the opposite end of the central portion. When implanted, the curvature of the shunt substantially corresponds to the exterior curvature of the eye at the location of the portion of the sclera at and adjacent to the limbus. The overall length of the shunt is sufficient to allow the anterior tab to extend intracorneally and the posterior tab to extend between the sclera and the choroid.

In a further embodiment the invention is directed to a method for treating glaucoma. The method includes forming an opening into the anterior chamber of the eye at the location of the limbus. The shunt is disposed onto the eye so as to bridge the opening. The anterior end of the shunt is disposed intracorneally and the posterior end of the shunt is disposed between the sclera and the choroid. The shunt is secured upon the eye by stitching. When implanted in this manner, fluid flows from the anterior chamber to the suprachoroidal space and is absorbed.

BRIEF DESCRIPTION OF THE DRAWINGS

FIG. 1b is a bottom view of the ophthalmic shunt shown in FIG. 1a.

FIG. 2b is a close-up side internal view of a portion of the eye shown in FIG. 2a.

FIG. 6b is a bottom view of the ophthalmic shunt shown in FIG. 6a.

FIGS. 6c and 6d are cross-sectional views of the ophthalmic shunt taken along line c—c in FIG. 6a.

DESCRIPTION OF THE PREFERRED EMBODIMENTS

Figure 1A:
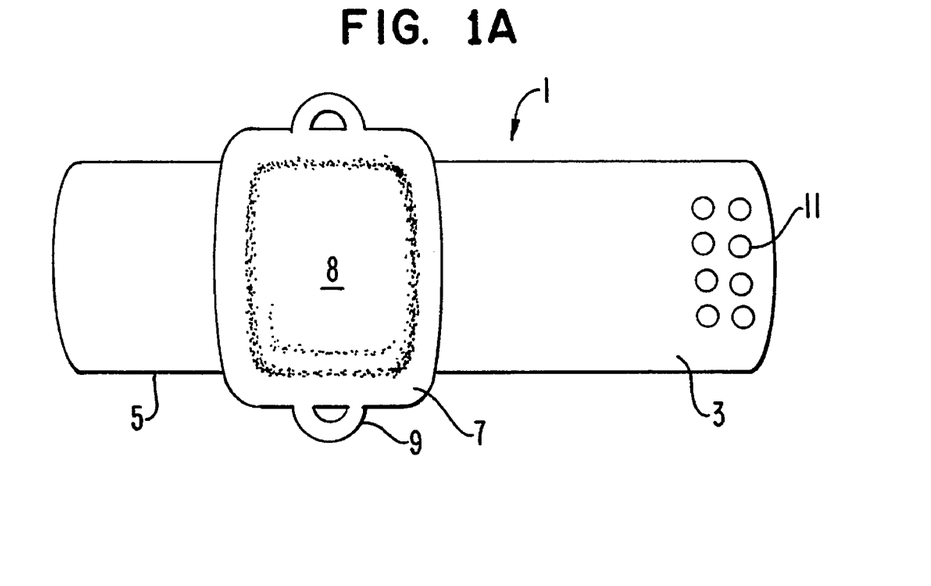
FIG. 1a is an overhead view of an ophthalmic shunt according to the invention.
Figure 1B:
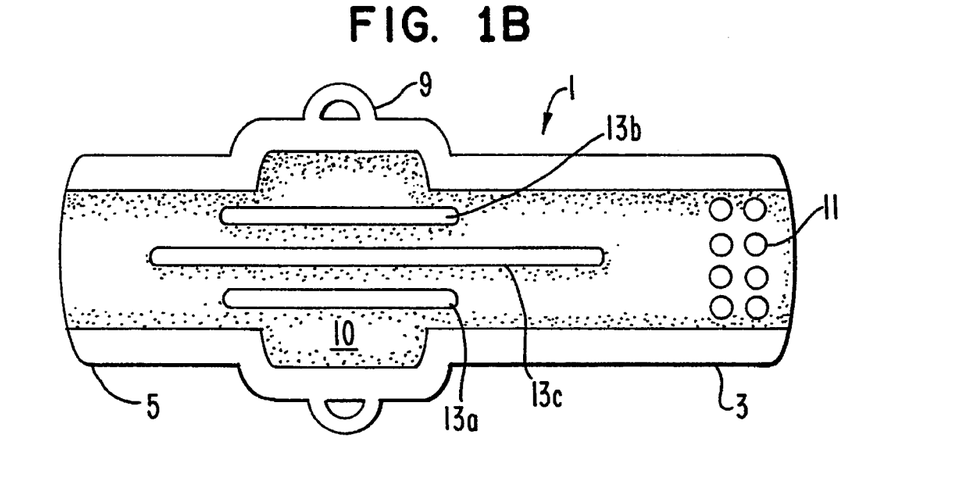
Figure 1C:
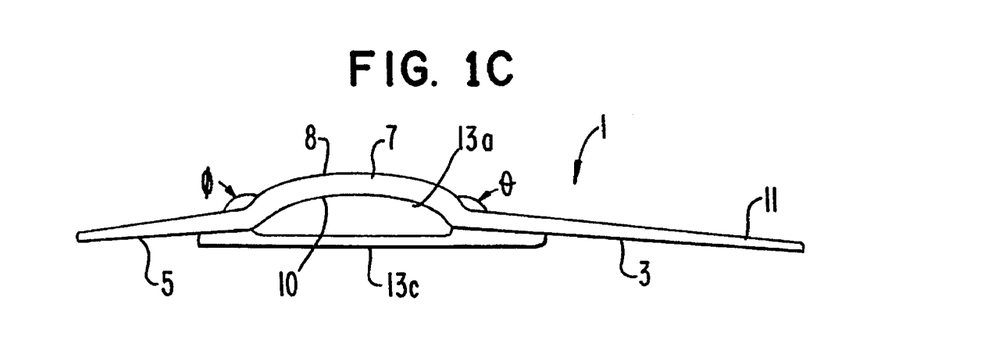
FIG. 1c is a side view of the ophthalmic shunt shown in FIG. 1a–b.

With reference to FIGS. 1a–1c, shunt 1 according to the invention is shown. Shunt 1 includes central portion 7, anterior tab 3 and posterior tab 5. Central portion 7 may have a rounded rectangular shape and is curved about a lateral axis so as to form convex surface 8 when viewed from above as in FIG. 1a, and concave surface 10 when viewed from below as in FIG. 1b. When implanted, the curvature of central portion 7 generally corresponds to the exterior curvature of the eye at the location of the limbus, with concave surface 10 disposed adjacent the sclera of the eye. Accordingly, for purposes of description, convex surface 8 may be referred to as the outer or exterior surface and concave surface 10 may be referred to as the inner or interior surface. A plurality of support walls or fins 13 extend inwardly from concave surface 10. Walls 13 help maintain the shape of shunt 1 when inserted in the eye, and also maintain a space between shunt 1 and the outer surface of the eye. As shown, shunt 1 may include three walls 13. Outer walls 13a–b extend along the entire length of central portion 7, and middle wall 13c is longer than outer walls 13a–b and extends for about one half the length of tabs 3 and 5. Stitching loops 9 extend laterally outwardly from the sides of central portion 7.

Tabs 3 and 5 may be formed at an angle to central portion 7, that is, a longitudinal axis of the tabs may not extend tangentially to the curved surface generally defined by central portion 7. Instead, such an axis would intersect the curved surface. These angles are shown as θ and φ in FIG. 1c. Further, the tabs are slightly curved about a longitudinal axis to present a smooth, convex exterior surface. Anterior tab 3 has a forward rounded end, and is beveled so as to decrease in thickness towards the forward end. Tab 3 includes a plurality of through-holes 11. Posterior tab 5 also is rounded. Preferably, shunt 1 is wider at central portion 7 than at tabs 3 and 5, and anterior tab 3 is longer than central portion 7 which is longer than posterior tab 5.

Shunt 1 is made of a semi-rigid but flexible material. In particular, the material and structure of shunt 1 must be rigid enough to allow the shunt to maintain its shape when implanted into an eye. As described further below, the shunt must be rigid enough to maintain a gap adjacent an opening formed in the limbus to allow fluid flow from the anterior chamber. However, the shunt also must be sufficiently soft and flexible to allow it to fit closely against the contours of the globe of the eye upon which it will be disposed, and to be implanted intracorneally. In a preferred embodiment, the material should have a SHORE A durometer reading of approximately 61, as well as a high tear strength above 250 psi, a high tensile strength above 1300 and a specific gravity of about 1.20. One suitable material is a medical grade liquid silicone rubber, for example, a millable implantable two-part silicone elastomer sold under the name SILASTIC®Q7-4765 AVE by Dow Corning. The shunt can be made by a conventional liquid injection molding or transfer molding process.

With reference to FIGS. 2a–4, the manner in which shunt 1 is implanted into human eye 20 will be explained. First incision or slit 37 is made through sclera 30 at a location rearward of limbus 40, that is, posterior to the region of sclera 30 at which the opaque white sclera starts to become clear cornea 24. First slit 37 is made completely through sclera 30 and extends to the outer surface of choroid 32. To avoid damage to retina 34, first slit 37 is made forward thereof in an area known as the pars planar. Preferably, slit 37 is made about 8 mm rearward of limbus 40.

Figure 2A:
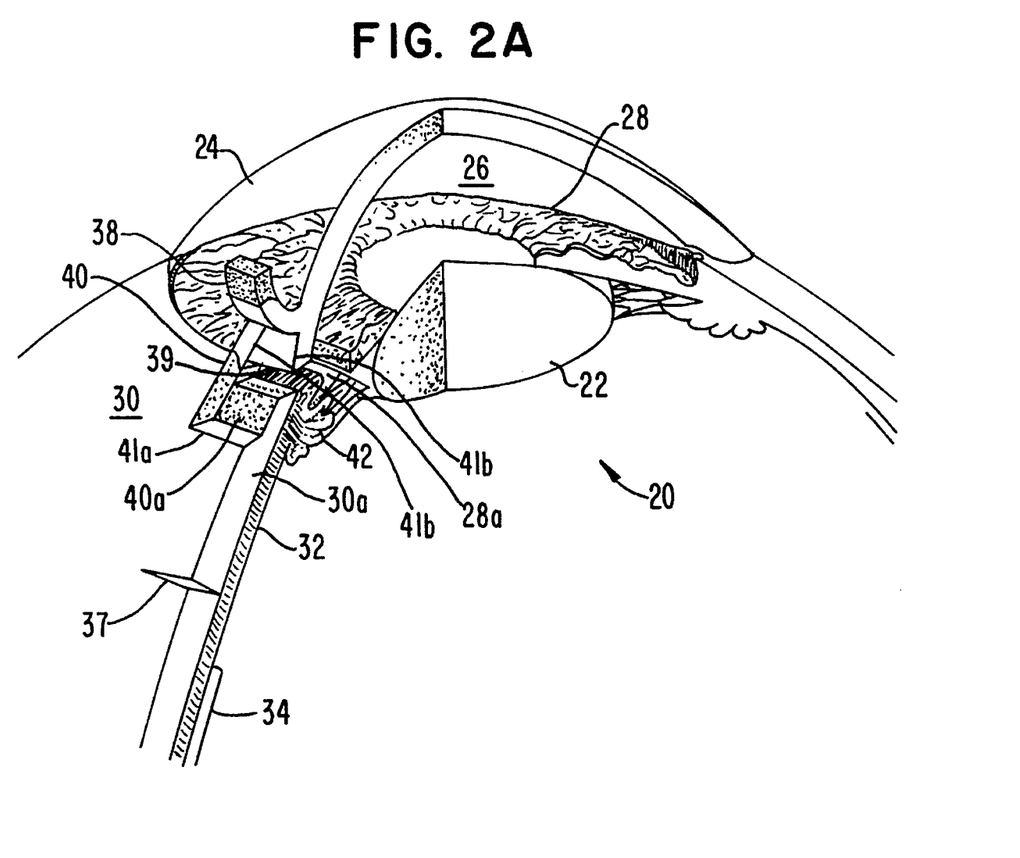
FIG. 2a is a cut-away perspective view of a human eye being prepared for implantation of a shunt according to the invention.
Figure 2B:
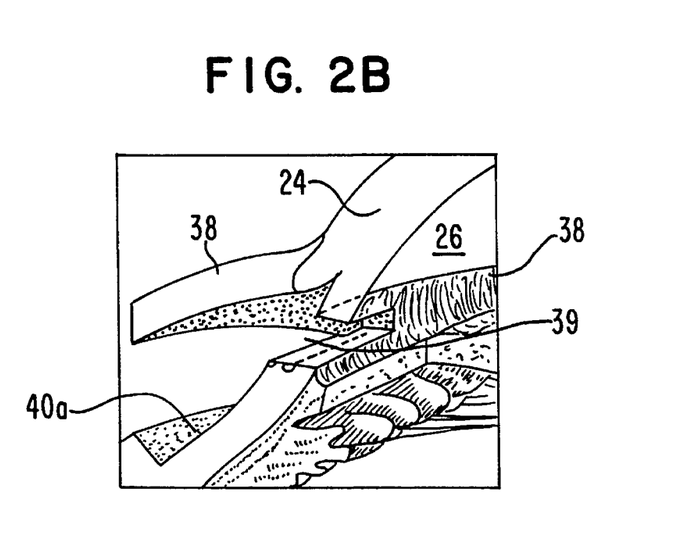

A second incision is made partially through sclera 30 at the general location of limbus 40. The second incision includes cut 41a, extending generally tangentially for a short distance along and approximately 4 mm posterior of limbus 40, and cuts 41b extending perpendicular to cut 41a, towards and into the outer layer of cornea 24 at the periphery. Cuts 41b extend partially through the thickness of sclera 30 and cornea 24, and do not extend into the inner corneal or scleral layers. In particular, cuts 41a do not extend into the endothelial cells layer of cornea 24. For example, cuts 41b may extend only half way through cornea 24. Cuts 41a and 41b define rectangular flap 38 including tissue of sclera 30 and cornea 24 at the general location of limbus 40.

Flap 38 is pulled back over the outer layer of cornea 24 to expose rectangular excised internal limbus region 40a from which the outer layers of sclera 30 and cornea 24 have been reflected. Preferably, cut 41a is formed about 4 mm forward of incision 37 and has a width of 4.5 mm, and cuts 41b have a length of 4.5 min. Excised region 40a would have approximately the same dimensions. Of course, these dimensions are approximate and will vary depending upon the particular situation encountered during surgery.

Additional third incisions are made through limbus 40 at excised region 40a, at a position slightly forward of ciliary body 42. These incisions extend through the remaining tissue at excised region 40a and define a generally rectangular region. When the tissue of limbus 40 defined within the third incisions is removed, rectangular opening 39 known as a sclerostomy is formed and extends into anterior chamber 26. Opening 39 allows communication between anterior chamber 26 and the exterior of eye 20. Opening 39 has a width slightly smaller than that of cut 41a, and extends perpendicularly a length of 2–3 min. An iridectomy is performed at the interior of opening 39 to form opening 28a through iris 28. The removal of a portion of iris 28 ensures that the iris will not block opening 39.

Figure 3:
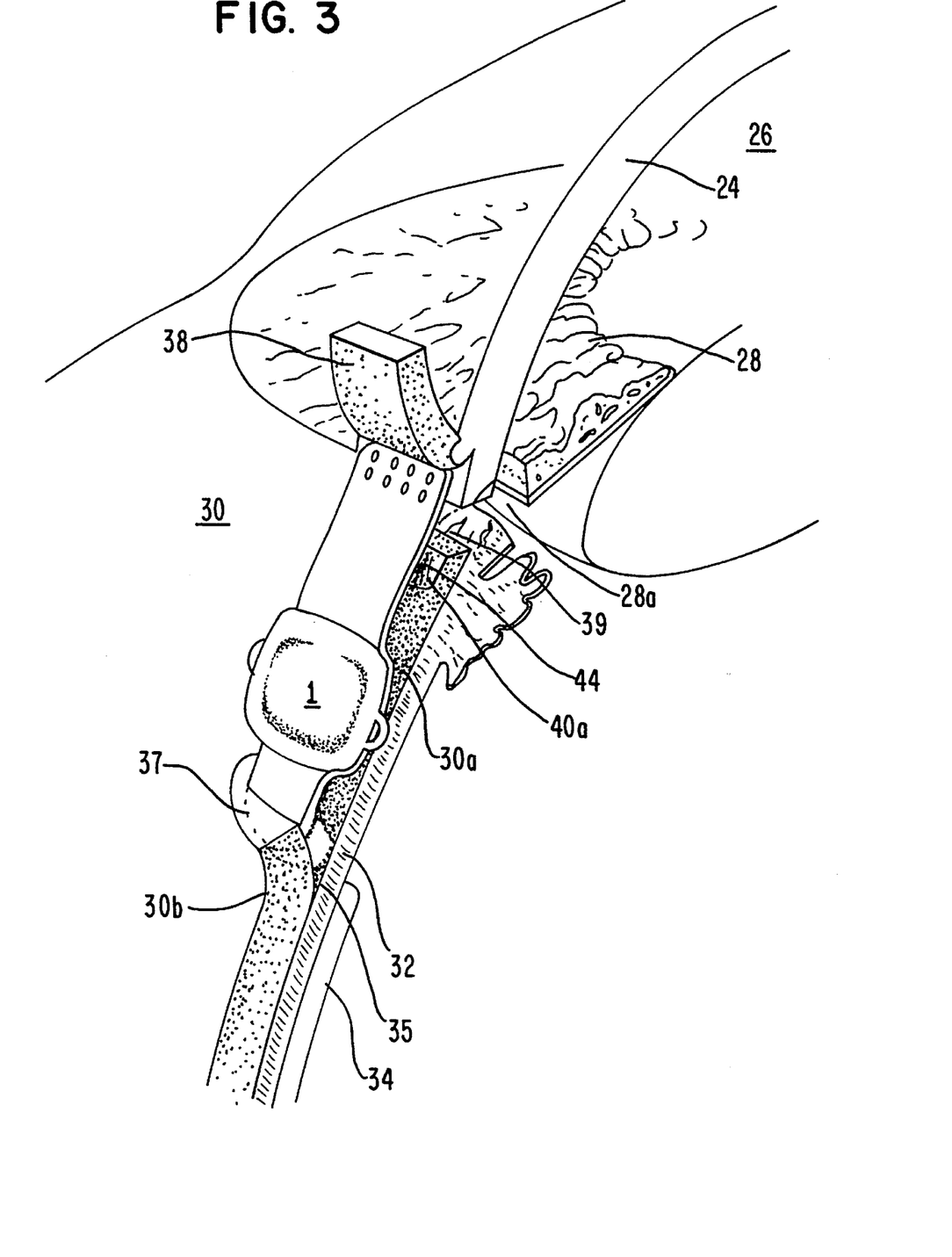
FIG. 3 is a cut-away perspective view of the implant shown in FIG. 1a–c as it is being implanted in a human eye.
Figure 5:
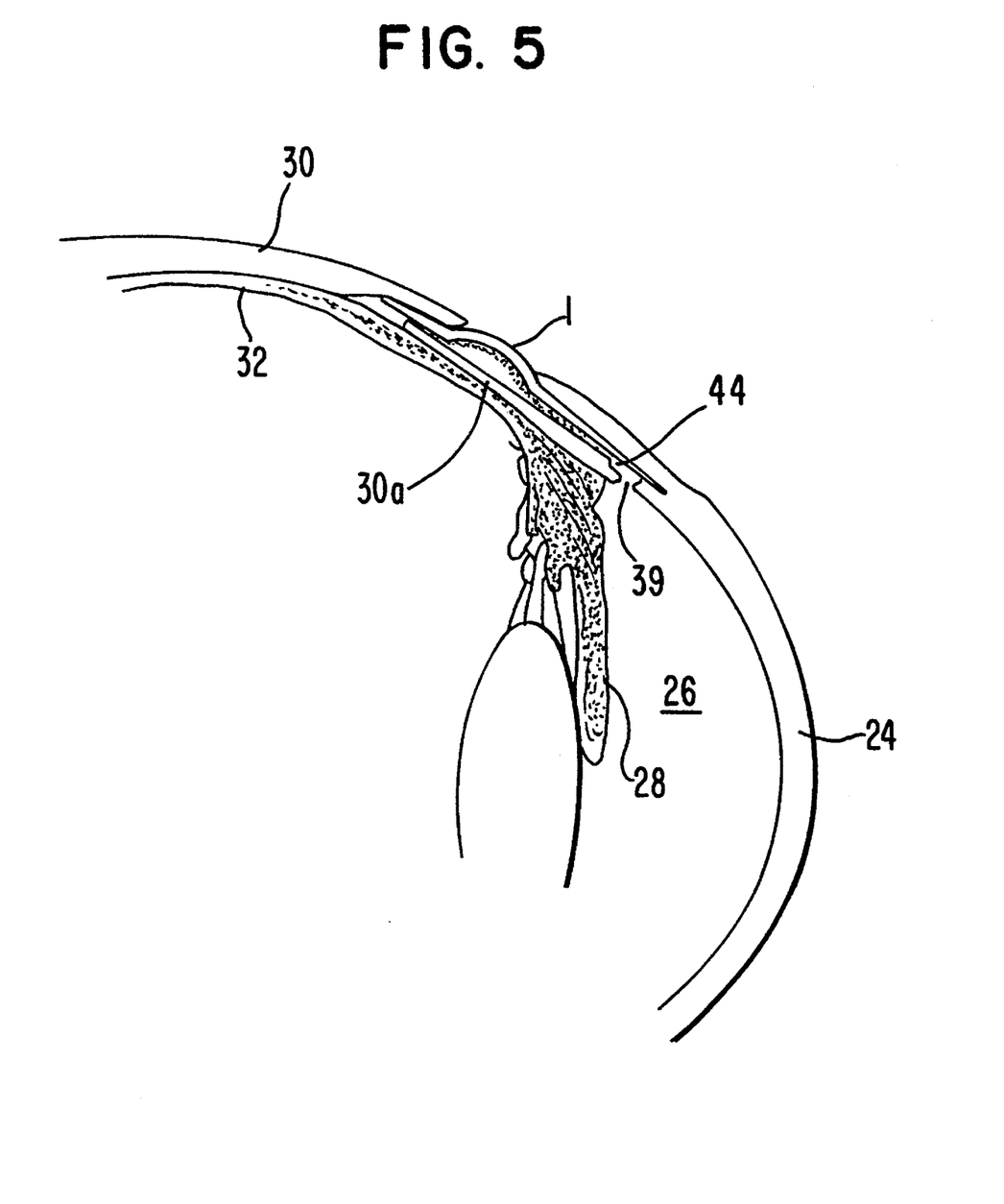
FIG. 5; is a partial cross-sectional view of an eye having an implant disposed therein.

Shunt 1 is implanted into eye 20 by inserting posterior tab 5 through slit 37 and between the inner surface of sclera 30 and the outer surface of choroid 32. The presence of tab 5 causes sclera 30 to be slightly raised at scleral portion 30b, forming suprachoroidal space 35 between sclera 30 and choroid 32. Space 35 is maintained due to the semi-rigidity of tab 5 and the fact that tab 5 has a convex outer surface. Central portion 7 and part of anterior tab 3 are disposed over section 30a of sclera 30 which remains between slit 37 and excised region 40a. Due to the angle between tabs 3 and 5 and central portion 7, the curvature of the tabs and central portion 7 and the overall flexibility of the shunt, when the shunt is implanted central portion 7 and tab 3 extend substantially above and parallel to and are spaced from the outer surface of sclera 30 at section 30a, with the curvature of shunt 1 substantially corresponding to the exterior curvature of the eye at and adjacent the location of the limbus. Each of the flexibility of the shunt, the angling of tabs and the curvature of the sections contribute to the capability of shunt 1 to generally conform to the shape of the eye when implanted.

Figure 4:
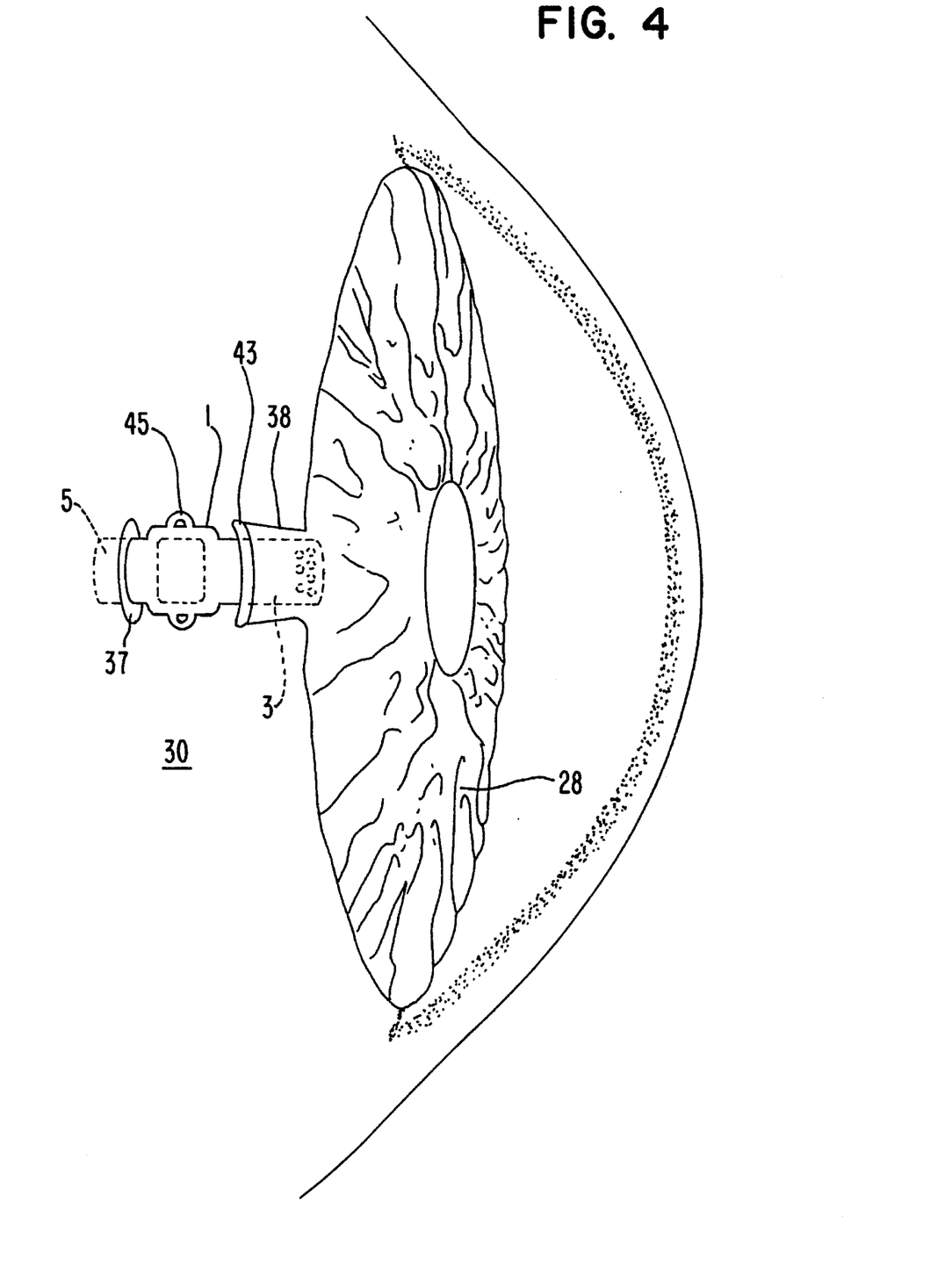
FIG. 4 is a simplified top surface view of a portion of the eye showing the implant disposed in the eye.

Anterior tab 3 extends slightly forwardly over excised region 40a and opening 39. Anterior tab 3 is disposed over the corneal portion of excised region 40a, that is, within the excised region of the cornea. Accordingly, shunt 1 bridges opening 39. Flap 38 is folded back rearwardly, and is secured in position over anterior tab 3 by stitches 43. Stitches 43 are disposed generally at limbus 40. Shunt 1 is secured in place by stitches 45, which extend through stitching loops 9, and into sclera 30.

When shunt 1 is implanted, gap 44 is formed between the lower surface 10 of shunt 1 and sclera 30 due to the removed portion of sclera 30 at excised region 40a. Gap 44 extends above opening 39, due to the angle made between anterior tab 3 and central portion 7, and the convex outer surface of tab 3. In other words, the structure of shunt 1 ensures that opening 39 will not be sealed by the shunt itself. By bridging opening 39 in this manner, shunt 1 allows aqueous humor to flow from anterior chamber 26 to reduce the pressure therein. The fluid flows along the lower surface of anterior tab 3 and interior surface 10 and into suprachoroidal space 35 where the fluid is absorbed and removed from the eye by normal processes. Due to the intracorneal positioning of anterior tab 3, contact with the sensitive endothelial layer of cornea 24 is avoided. Thus, shunt 1 according to the invention will not damage the cornea. Further, the provision of through holes 11 in tab 3 allows the outer corneal layers to be nourished, avoiding damage to these layers.

Shunt 1 is stably positioned intracorneally at one end, and extends to a suprachoroidal space at the other end. The shunt bridges an opening into the eye, and is disposed close to but spaced from the exterior surface of the sclera. Thus, fluid flow from the anterior chamber to the suprachoroidal space is made possible and damage to the cornea is avoided. In one embodiment, the overall length of shunt 1 may be approximately 8–11 mm and preferably 10 mm, with anterior tab 3 having a length of 3–4.5 mm and preferably 4.5 mm and a width of 3 mm, central portion 7 having a length of 3–4 mm and preferably 3 mm, and a width of 3–5 mm and preferably 4 mm, and posterior tab 5 having a length of 2–3 mm and preferably 2.5 mm and a width of 3 mm. Shunts having differing lengths and widths to correspond to variations in the dimensions of the eye are possible.

With reference to FIGS. 6a–d, a second embodiment of the invention is shown. Shunt 100 has a similar construction to shunt 1 including central portion 107, anterior tab 103 having through holes 111, and posterior tab 105. Solid walls 106 extend downwardly from the lower surface of shunt 100 and extend longitudinally along both sides of shunt 100 from anterior tab 103 to posterior tab 105. Walls 106 define central longitudinal channel 108 extending the entire length of shunt 100. Circular threaded opening 110 is formed through central portion 107, and extends through solid walls 106. Solid screw-threaded cylindrical barrier 102 is disposed within opening 110 and includes head 102a having slot 102b. The relative vertical position of barrier 102 may be adjusted within opening 110 by use of a flat-edge tool in a conventional manner.

Figure 6A:
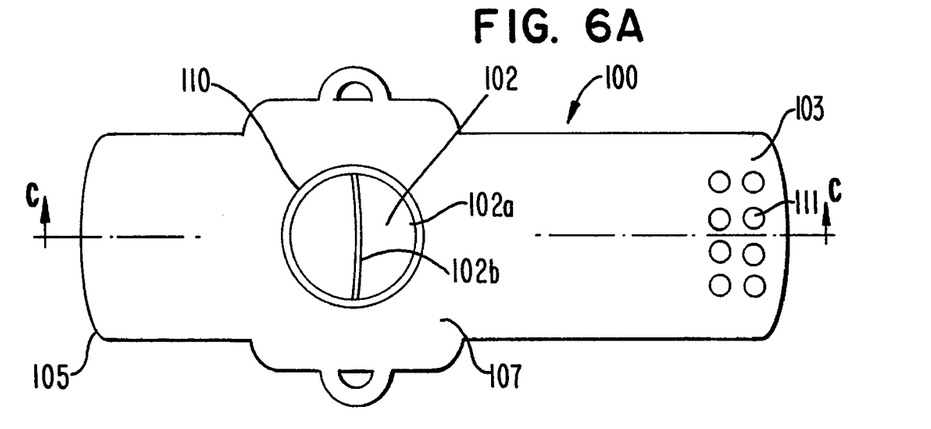
FIG. 6a an overhead view of an ophthalmic shunt according to a second embodiment of the invention.
Figure 6B:
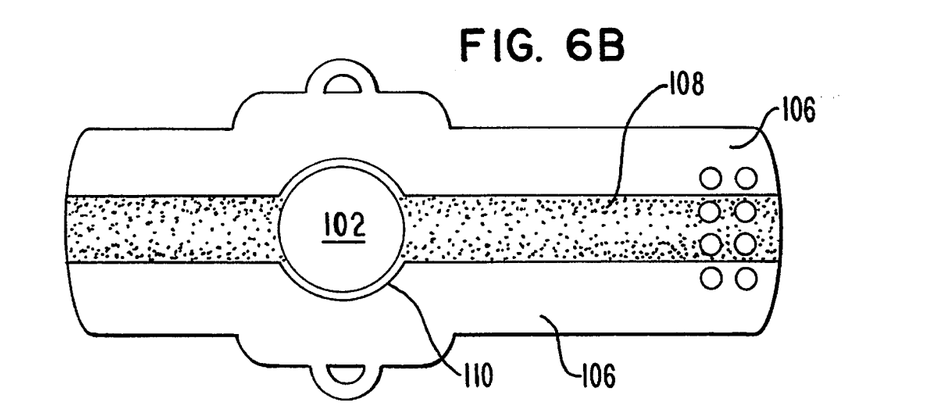
Figure 6C:
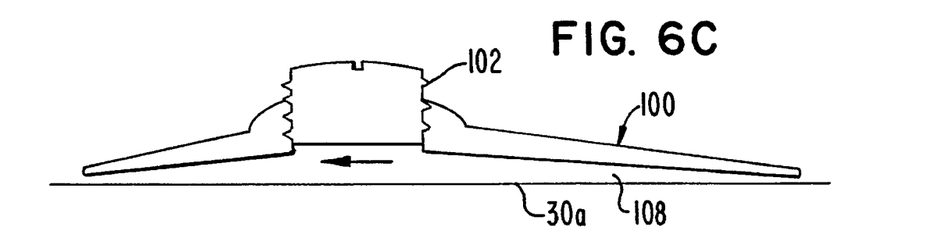
Figure 6D:
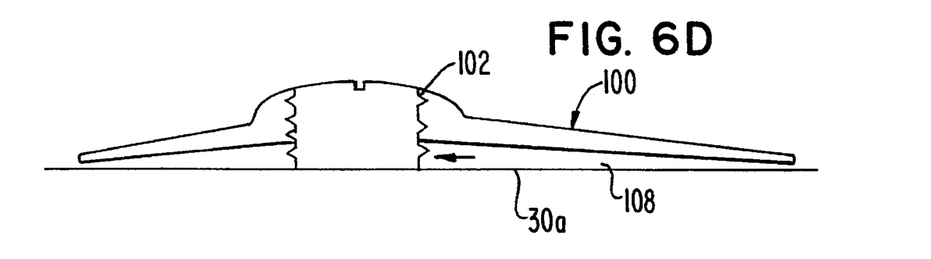

Shunt 100 is implanted within the eye in the same manner as described with respect to shunt 1. The lower surfaces of solid walls 106 will be in substantial contact with the outer surface of the eye, in particular, the outer surface of scleral section 30a, thereby restricting the flow of aqueous fluid such that it flows only through channel 108. The lower surface of the shunt at the location of channel 108 will be spaced from the outer surface of scleral section 30a. The rate of fluid flow through channel 108 may be adjusted by adjusting the vertical position of barrier 102. For example, if barrier 102 is raised to the uppermost position as shown in FIG. 6c, channel 108 is completely open, and maximum fluid flow through channel 108 will be permitted. By disposing barrier 102 in an intermediate position, an intermediate rate of fluid flow will be permitted. If barrier 102 is in its lower-most position as shown in FIG. 6d, the lower surface of barrier 102 will be in contact with the surface of scleral portion 30a, blocking channel 108. Accordingly, fluid flow through channel 108 and thus shunt 100 will be substantially precluded.

This invention has been described in detail in connection with the preferred embodiments. These embodiments, however, merely are for example only and the invention is not restricted thereto. It will be understood by those skilled in the art that other variations and modifications can easily be made within the scope of this invention as defined by the claims.

I claim:

1. An ophthalmic shunt implantable in a human eye, the eye having a sclera, a limbus, a cornea and a choroid, wherein the shunt consists essentially of:

a central portion exhibiting a convex outer surface, a concave inner surface and sides;

an anterior tab with a smooth exterior surface extending along a longitudinal axis from one end of said central portion;

a posterior tab with a smooth outer surface extending along said longitudinal axis from an opposite end of said central portion;

a support wall projecting from said concave inner surface and extending along a longitudinal axis to maintain a shape of said shunt when inserted into an eye and to maintain a channel between said central portion and an outer surface of said eye; and stitching loops extending laterally outward from the sides of the central portion for securing said shunt to said eye.

2. The shunt recited in claim 1, wherein, said shunt is made of a flexible material and said central portion is curved, the curvature and flexibility of said shunt allowing it to assume a curvature when implanted which substantially corresponds to the exterior curvature of the eye.

3. The shunt recited in claim 2, said anterior tab and said posterior tab disposed at an angle to said central portion, wherein, the flexibility of the material allows said anterior tab to be implanted intracorneally with the material having a rigidity sufficient to maintain a gap above an opening formed through the limbus.

4. The shunt recited in claim 2, said material having a SHORE A durometer reading of approximately 61.

5. The shunt recited in claim 2, the material comprising medical grade liquid silicone rubber.

6. The shunt recited in claim 2, wherein, said posterior tab is rounded about a longitudinal axis, and said anterior tab tapers to a diminishing thickness.

7. The shunt recited in claim 1, said shunt having tin overall length of 8–11 mm and a maximum width at said central portion of between 3–5 mm.

8. The shunt recited in claim 1, said central portion having a length of 3–4 mm, said anterior tab having a length of 3–4.5 mm and said posterior tab having a length of 2–3 mm.

9. The shunt recited in claim 1 further comprising a valve disposed at said central portion, said valve controlling the flow of fluid along the lower surface of said shunt.

10. The shunt recited in claim 9 further including a pair of walls extending from the lower surface and defining a central longitudinal channel extending the entire length of said shunt, and an opening formed through said central portion and said walls, said valve comprising a positionally adjustable barrier disposed within said opening, wherein, the position of said barrier may be adjusted to control the flow of fluid through said central longitudinal channel.

11. The shunt recited in claim 10, said opening and said barrier including corresponding screw-threading.

12. A method for treating glaucoma by implantation of a shunt into an eye, the method comprising:

making a first incision extending through the sclera and to the outer surface of the choroid at a location substantially rearward of the limbus;

making a second incision extending partially through the sclera and cornea at the location of the limbus, the second incision defining a flap of tissue at the limbus;

pulling the flap over the outer layers of the cornea to expose an internal region of the limbus;

making third incisions through the internal region and removing a portion of the limbus to form an opening into the anterior chamber of the eye;

disposing a shunt exhibiting an anterior end and a posterior end upon the eye with a posterior end of the shunt inserted through said first incision to form a space between the choroid and sclera, and the anterior end of the shunt disposed upon the corneal tissue at the internal region such that the shunt bridges the opening;

pulling the flap over the anterior end of said shunt;

stitching the flap in place over the shunt; and stitching the shunt to the sclera.

13. The method recited in claim 12, further comprising:

forming an opening through the iris.

14. A method for treating glaucoma in an eye by the steps comprising:

forming an opening into an anterior chamber of the eye at the location of the limbus;

disposing a shunt exhibiting stitching loops a convex outer surface, a concave inner surface, an anterior end with a smooth outer surface, and a posterior end with a smooth outer surface onto the eye so as to bridge the opening, with the anterior end of the shunt disposed intracorneally and the posterior end of the shunt disposed between the sclera and the choroid; and securing the shunt to the eye by stitching the stitching loops to the eye.

15. The method recited in claim 14, wherein, the disposing step further includes pulling back the outer corneal layers so as to allow the anterior end of the shunt to be disposed intracorneally.

16. The method recited in claim 14, wherein the disposing step further includes making an incision through the sclera posteriorly of Where the opening is formed, and disposing a posterior end of the shunt through the incision to form a suprachoroidal space.

* * * * *